(12) United States Patent
Jiaang et al.

(10) Patent No.: US 10,300,061 B2
(45) Date of Patent: May 28, 2019

(54) AMINOTHIAZOLE COMPOUNDS AS PROTEIN KINASE INHIBITORS

(71) Applicant: National Health Research Institutes, Miaoli County (TW)

(72) Inventors: Weir-Torn Jiaang, Taipei (TW); Chuan Shih, Carmel, IN (US); Hui-Jen Tsai, Kaohsiung (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 16/007,417

(22) Filed: Jun. 13, 2018

(65) Prior Publication Data

US 2018/0353509 A1    Dec. 13, 2018

Related U.S. Application Data

(60) Provisional application No. 62/518,855, filed on Jun. 13, 2017.

(51) Int. Cl.
| | | |
|---|---|---|
| *C07D 417/14* | (2006.01) | |
| *A61K 31/5377* | (2006.01) | |
| *A61K 31/506* | (2006.01) | |
| *A61P 35/00* | (2006.01) | |

(52) U.S. Cl.
CPC ........ *A61K 31/506* (2013.01); *A61K 31/5377* (2013.01); *A61P 35/00* (2018.01)

(58) Field of Classification Search
CPC . C07D 417/14; A61K 31/5377; A61K 31/506
See application file for complete search history.

(56) References Cited

U.S. PATENT DOCUMENTS

2008/0125440 A1    5/2008  Cal et al.

FOREIGN PATENT DOCUMENTS

| CN | 106279143 A | 1/2017 |
|---|---|---|
| WO | WO-2004/041164 A2 | 5/2004 |
| WO | WO-2007/141571 A2 | 12/2007 |
| WO | WO-2008/150446 A1 | 12/2008 |
| WO | WO-2018/106643 A1 | 6/2018 |

OTHER PUBLICATIONS

Christopher et al., Drug Metabolism and Disposition, vol. 36, No. 7, pp. 1357-1364, 2008.*
Pubmed Compound Summary for CID 108777084, "RYLSWZAXLWZDPI-UHFFFAOYSA-N" U.S. National Library of Medicine, pp. 1-9, 2016.

* cited by examiner

*Primary Examiner* — Rebecca L Anderson
(74) *Attorney, Agent, or Firm* — Cesari and McKenna, LLP

(57) ABSTRACT

Aminothiazole compounds of Formula (I) shown below and pharmaceutical compositions containing one of such compounds:

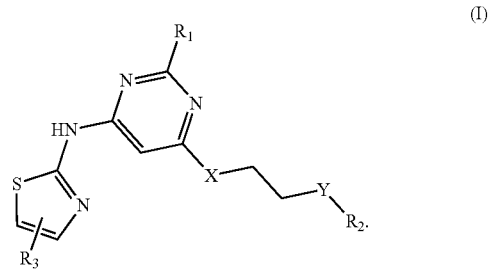

(I)

Also disclosed are methods of inhibiting a tyrosine kinase and treating cancer associated with a tyrosine kinase with one of the aminothiazole compounds.

26 Claims, No Drawings

AMINOTHIAZOLE COMPOUNDS AS PROTEIN KINASE INHIBITORS

CROSS-REFERENCE TO RELATED APPLICATIONS

This application claims priority from U.S. provisional patent application No. 62/518,855, filed on Jun. 13, 2017.

BACKGROUND

Protein kinases are important in cellular signal pathways that regulate various cell functions, including differentiation, proliferation, migration, and apoptosis. Deregulation of protein kinases is implicated in cancer and a number of other diseases.

Tyrosine kinases, a subclass of protein kinases, regulate target protein function through transfer of phosphate from ATP to the hydroxyl group of a target protein tyrosine. FMS-like tyrosine kinase 3 ("FLT3"), vascular endothelial growth factor receptor ("VEGFR"), and tyrosine-protein kinase Kit ("c-Kit") are three tyrosine kinases that have been studied as attractive therapeutic targets in cancer treatment.

Mutations of FLT3, a receptor tyrosine kinase, can lead to development of cancer, e.g., acute myeloid leukemia. See Pratz et al., *Current Drug Targets*, 2010, 11(7), 781-9.

By binding to VEGFR and activating it via transphosphorylation, vascular endothelial growth factor, a signal protein, stimulates growth of new blood vessels. VEGFR has been identified as the predominant regulator of tumor angiogenesis. See Hicklin et al., *J Clin Oncol.*, 2005, 23, 1011-1027.

c-Kit, also a receptor tyrosine kinase, is involved in intracellular signaling. The mutated form of c-Kit plays a crucial role in occurrence of some cancers. Inhibition of c-Kit has proved to be effective in treating gastrointestinal stromal tumor, acute myeloid leukemia, and melanoma. See Babaei et al., *Drug Des Devel Ther.*, 2016 10, 2443-2459.

Aminothiazoles compounds, extensively explored as potent tyrosine kinase inhibitors, present several challenges as drug candidates. They possess poor kinase selectivity, often cause animal death in toxicity studies, and generally lack adequate in vivo exposure to exert desirable efficacy in pre-clinical or clinical studies.

There is a need to develop new aminothiazole compounds that specifically inhibit certain tyrosine kinases, demonstrate desirable safety profiles, and exert sufficient in vivo efficacy in treating target cancers.

SUMMARY

The present invention is based on unexpected discoveries that certain aminothiazole compounds effectively inhibit multiple tyrosine kinases, e.g., FLT3, VEGFR, and c-Kit.

In one aspect, this invention relates to aminothiazole compounds of Formula (I):

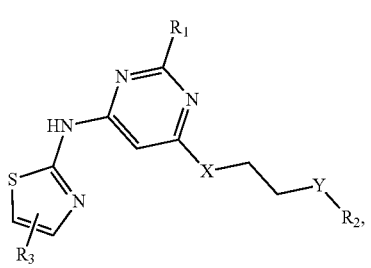

(I)

in which $R_1$ is $C_{1-6}$ alkyl or $C_{1-6}$ thioalkyl; X is O or $NR_a$, in which $R_a$ is H or $C_{1-6}$ alkyl; Y is $CR_bR_c$ or $NR_d$, in which each of $R_b$ and $R_c$, independently, is H, halo, $C_{1-6}$ alkyl, $C_{1-6}$ alkoxyl, or amino, or $R_b$, together with $R_a$, the carbon atom bonded to $R_b$, and the nitrogen atom bonded to $R_a$, is $C_{3-10}$ heterocycloalkyl, and $R_d$ is H or $C_{1-6}$ alkyl, or $R_d$, together with $R_a$ and the nitrogen atoms bonded to $R_d$ and $R_a$, is $C_{3-10}$ heterocycloalkyl; $R_2$ is —$CH_2CH_2R_e$ or $NR_fR_g$, in which $R_e$ is H, halo, $C_{1-6}$ alkyl, or $OR_h$, and each of $R_f$ and $R_g$, independently, is $C_{1-6}$ alkyl or $C_{3-8}$ cycloalkyl, $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; and $R_3$ is heteroaryl.

The term "alkyl" herein refers to a saturated, linear or branched hydrocarbon moiety, such as —$CH_3$ or branched —$C_3H_7$. The term "cycloalkyl" refers to a non-aromatic, monocyclic, bicyclic, tricyclic, or tetracyclic hydrocarbon moiety, such as cyclohexyl, cyclohexen-3-yl, or adamantyl. The term "alkoxyl" refers to an —O-alkyl radical. Examples of alkoxyl include, but are not limited to, methoxy, ethoxy, n-propoxy, isopropoxy, n-butoxy, iso-butoxy, sec-butoxy, and tert-butoxy. The term "thioalkyl" refers to an —S-alkyl radical. Examples of thioalkyl include, but are not limited to, methylthiol, ethylthiol, and benzylthiol. The term "heterocycloalkyl" refers to a non-aromatic, monocyclic, bicyclic, tricyclic, or tetracyclic moiety having one or more ring heteroatoms (e.g., N, O, or S). Examples of heterocycloalkyl include, but are not limited to, 4-morpholinyl, 1-piperazinyl, 4-tetrahydropyranyl, and 4-pyranyl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl, and indolyl.

Alkyl, thioalkyl, alkoxyl, cycloalkyl, heterocycloalkyl, and heteroaryl mentioned herein include both substituted and unsubstituted moieties, unless specified otherwise. Possible substituents on cycloalkyl, heterocycloalkyl, and heteroaryl include $C_{1-10}$ alkyl, $C_{2-10}$ alkenyl, $C_2$-10 alkynyl, $C_{3-20}$ cycloalkyl, $C_{3-20}$ cycloalkenyl, $C_{1-20}$ heterocycloalkyl, $C_{1-20}$ heterocycloalkenyl, $C_{1-10}$ alkoxy, aryl, aryloxy, heteroaryl, heteroaryloxy, amino, $C_{1-10}$ alkylamino, $C_1$-$_{20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The aminothiazole compounds described above include the compounds themselves, as well as their salts, prodrugs, and solvates, if applicable. A salt, for example, can be formed between an anion and a positively charged group (e.g., amino) on an aminothiazole compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an aminothiazole compound. Suitable cations include sodium ion, potassium ion, magnesium ion, calcium ion, and an ammonium cation such as tetramethylammonium ion. The aminothiazole compounds also include those salts containing quaternary nitrogen atoms. Examples of prodrugs include esters and other pharmaceutically acceptable derivatives, which, upon administering to a subject, are capable of providing active aminothiazole compounds. A solvate refers to a complex formed between an active aminothiazole compound and a pharmaceutically acceptable solvent. Examples of a pharmaceutically acceptable solvent include water, ethanol, isopropanol, ethyl acetate, acetic acid, and ethanolamine.

In another aspect, this invention relates to a method for inhibiting a tyrosine kinase, e.g., FLT3, VEGFR, and c-Kit. The method includes contacting the tyrosine kinase with an effective amount of one or more of the above-described aminothiazole compounds.

Also within the scope of this invention is a method for treating cancer associated with a tyrosine kinase. The method includes administering to a subject in need thereof an effective amount of one or more of the aminothiazole compounds of Formula (I) described above.

The tyrosine kinase associated to a cancer can be a wild type or mutant. Examples of the tyrosine kinase include, but are not limited to, FLT3, FLT4, VEGFR, platelet-derived growth factor receptor (PDGFR) A, PDGFR B, c-Kit, c-Src (SRC), tyrosine-protein kinase Lyn (LYN) A, LYN B, rearranged during transfection tyrosine kinase (RET), lymphocyte-specific protein tyrosine kinase, Gardner-Rasheed feline sarcoma viral oncogene homolog, discoidin domain receptor 1, kinase insert domain receptor, B lymphocyte kinase, tyrosine-protein kinase Yes, Abelson murine leukemia viral oncogene homolog 1 (ABL1), tyrosine-protein kinase Tek, RET V804L, RET Y791F, FLT3 D835Y, PDGFR A V561D, or ABL1 T315I.

In an exemplary method, the aminothiazole compounds of Formula (I) are used for treating cancer associated with FLT3, VEGFR, or c-Kit.

Examples of the cancer include acute myeloid leukemia, chloroma, chronic myelogenous leukemia, acute lymphoblastic leukemia, chronic lymphocytic leukemia, Hodgkin's disease, non-Hodgkin's lymphoma, B-cell lymphoma, multiple myeloma, Waldenstrom's macroglobulinemia, myelodysplastic syndrome, pancreatic cancer, bladder cancer, colorectal cancer, breast cancer, male genital tract cancer, renal cancer, hepatocellular cancer, lung cancer, ovarian cancer, cervical cancer, uterus cancer, gestational trophoblastic disease, gastric cancer, bile duct cancer, gallbladder cancer, small intestine cancer, esophageal cancer, oropharyngeal cancer, hypopharyngeal cancer, eye cancer, nerve cancer, head and neck cancer, melanoma, plasmacytoma, endocrine gland neoplasm, neuroendocrine cancer, brain tumor, bone cancer, and sarcoma (e.g., gastrointerstinal stromal tumor or GIST).

Further within the scope of this invention is a pharmaceutical composition containing one or more of the above-described aminothiazole compounds of Formula (I). The pharmaceutical composition can be used for treating cancer.

This invention also encompasses use of one or more of the above-described aminothiazole compounds of Formula (I) for the manufacture of a medicament for treating cancer.

The term "treating" or "treatment" refers to administering one or more of the aminothiazole compounds to a subject, who has an above-described disease, i.e., cancer, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

To practice the method of the present invention, a composition having one or more of the above-described aminothiazole compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more of the above-described aminothiazole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed in detail are aminothiazole compounds of Formula (I):

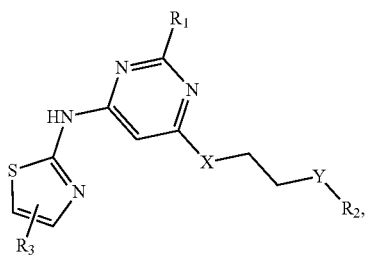
(I)

in which variables $R_1$, $R_2$, $R_3$, X, and Y are defined in the SUMMARY section above.

Typically, compounds of Formula (I) have $R_3$ being 5- or 6-membered heteroaryl substituted with one or more $(CH_2)_n Z$ moieties independently, in which n is 0 or 1 and Z is H, halo, CN, OH, $CF_3$, $C_{1-6}$ alkyl, or $C_{1-6}$ alkoxyl; or have $R_3$ being 5- or 6-membered heteroaryl fused with a phenyl ring substituted with one or more substituents independently selected from the group consisting of H, halo, CN, OH, $CF_3$, $C_{1-6}$ alkyl, and $C_{1-6}$ alkoxyl. Exemplary compounds have $R_3$ being 6-membered heteroaryl substituted with one or more $(CH_2)_n Z$ moieties independently, in which n is 0 or 1 and Z is H, halo, CN, OH, $CF_3$, $C_{1-6}$ alkyl, or $C_{1-6}$ alkoxyl. Two examples of $R_3$ are pyridyl and pyrimidyl.

A group of the above-described novel aminothiazole compounds are compounds of Formula (II):

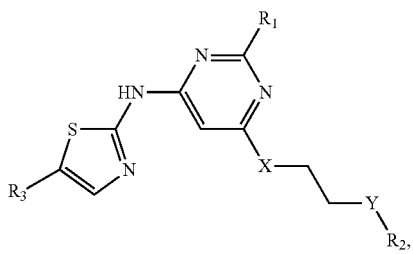
(II)

in which $R_1$ is $C_{1-6}$ alkyl.

In one subset, compounds of Formula (II) have X being O, Y being $NR_d$, and $R_2$ being —$CH_2CH_2R_e$, in which $R_e$ is $OR_h$, $R_h$, together with $R_d$, the oxygen atom bonded to $R_h$, and the nitrogen atom bonded to $R_d$, being $C_{3-10}$ heterocycloalkyl. Compounds of this subset can have $R_3$ being 5- or 6-membered heteroaryl substituted with one or more $(CH_2)_n Z$ moieties independently, in which n is 0 or 1 and Z is H, halo, CN, OH, $CF_3$, $C_{1-6}$ alkyl, or $C_{1-6}$ alkoxyl; or is 5- or 6-membered heteroaryl fused with a phenyl ring substituted with one or more substituents independently selected from H, halo, CN, OH, $CF_3$, $C_{1-6}$ alkyl, and $C_{1-6}$ alkoxyl. For example, $R_3$ can be pyridyl or pyrimidyl. Exemplary compounds include, but are not limited to, the following compounds:

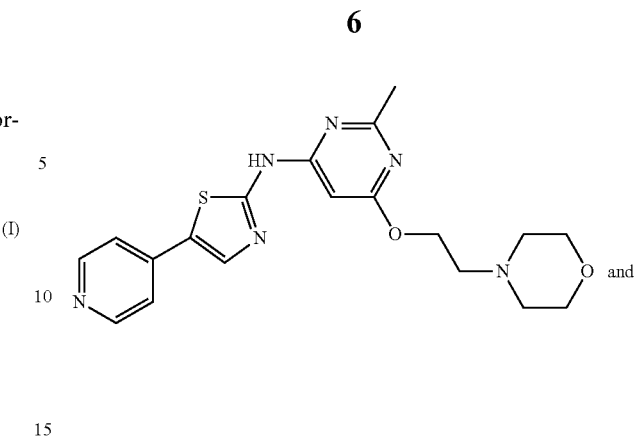
and

In another subset, compounds of Formula (II) have X being $NR_a$ and Y being $CR_bR_c$ or $NR_d$, in which $R_a$, together with $R_b$, the nitrogen atom bonded to $R_a$, and the carbon atom bonded to $R_b$, is $C_{3-10}$ heterocycloalkyl; $R_c$ is H, halo, $C_{1-6}$ alkyl, $C_{1-6}$ alkoxyl, or amino; and $R_d$, together with $R_a$ and the nitrogen atoms bonded to $R_a$ and $R_d$, is $C_{3-10}$ heterocycloalkyl.

Of note, these compounds can have X being $NR_a$, Y being $CR_bR_c$, and $R_2$ being $NR_fR_g$, in which $R_a$, together with $R_b$, the nitrogen atom bonded to $R_a$, and the carbon atom bonded to $R_b$, is $C_{3-10}$ heterocycloalkyl; $R_c$ is H, halo, $C_{1-6}$ alkyl, $C_{1-6}$ alkoxyl, or amino; and each of $R_f$ and $R_g$ is $C_{1-6}$ alkyl. They typically have $R_3$ being 5- or 6-membered heteroaryl substituted with one or more $(CH_2)_n Z$ moieties independently, in which n is 0 or 1 and Z is H, halo, CN, OH, $CF_3$, $C_{1-6}$ alkyl, or $C_{1-6}$ alkoxyl; or is 5- or 6-membered heteroaryl fused with a phenyl ring substituted with one or more substituents independently selected from H, halo, CN, OH, $CF_3$, $C_{1-6}$ alkyl, and $C_{1-6}$ alkoxyl. $R_3$ can be pyridyl or pyrimidyl. Exemplary compounds include, but are not limited to, the following compounds:

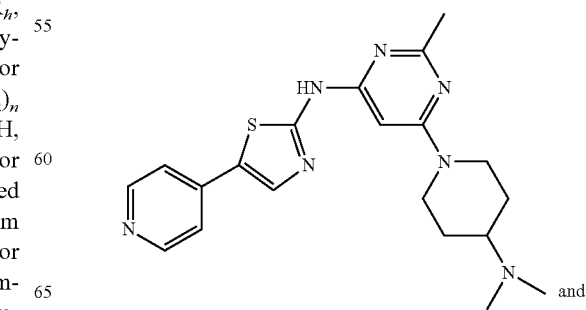
and

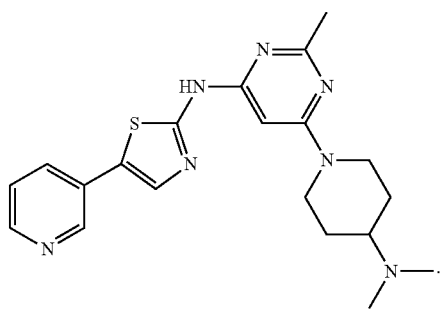

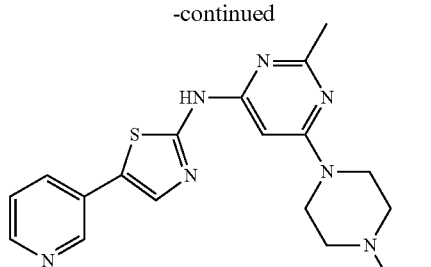

On the other hand, the compounds in this subset can have X being $NR_a$, Y being $NR_d$, and $R_2$ being —$CH_2CH_2R_e$, in which $R_a$, together with $R_d$ and the nitrogen atoms bonded to $R_a$ and $R_d$, is $C_{3-10}$ heterocycloalkyl; and $R_e$ is H, halo, or $OR_h$, $R_h$ being H or $C_{1-6}$ alkyl. In general, these compounds have $R_3$ being 5- or 6-membered heteroaryl substituted with one or more $(CH_2)_nZ$ moieties independently, in which n is 0 or 1 and Z is H, halo, CN, OH, $CF_3$, $C_{1-6}$ alkyl, or $C_{1-6}$ alkoxyl; or is 5- or 6-membered heteroaryl fused with a phenyl ring substituted with one or more substituents independently selected from H, halo, CN, OH, $CF_3$, $C_{1-6}$ alkyl, and $C_{1-6}$ alkoxyl. For instance, $R_3$ is pyridyl or pyrimidyl. Exemplary compounds include, but are not limited to, the following compounds:

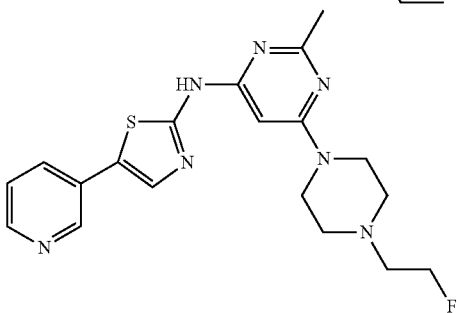

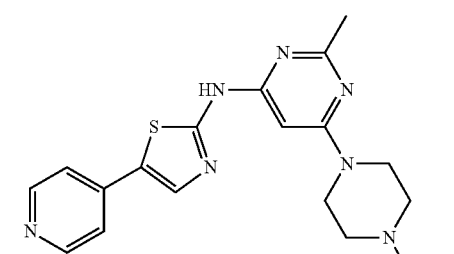

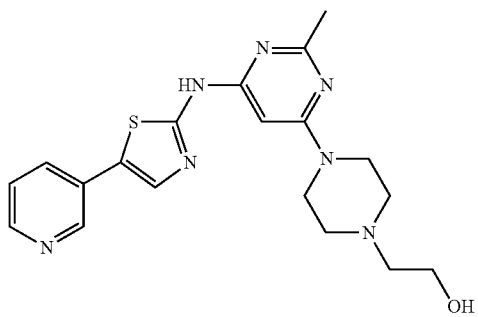

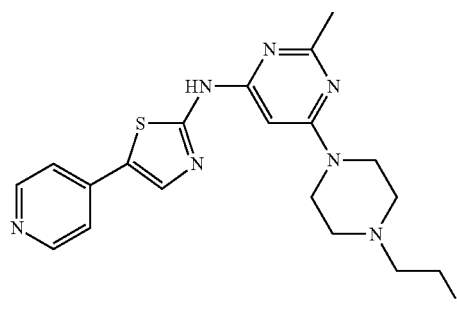

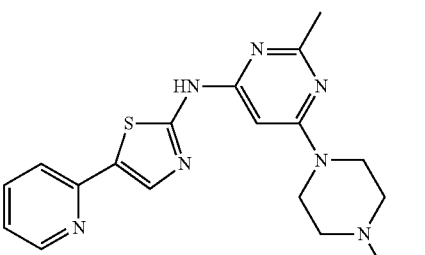

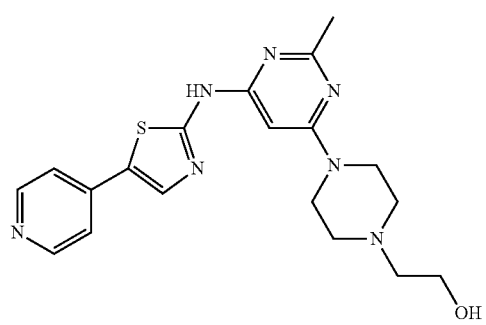

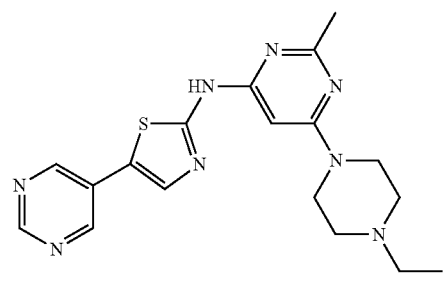

Another group of the novel aminothiazole compounds set forth above are compounds of Formula (III):

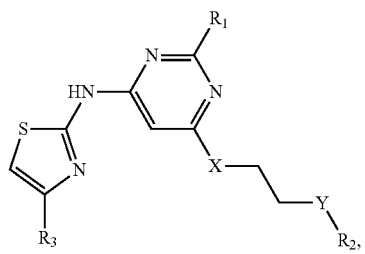
(III)
in which $R_1$ is $C_{1-6}$ alkyl.
An exemplary compound of formula (III) is
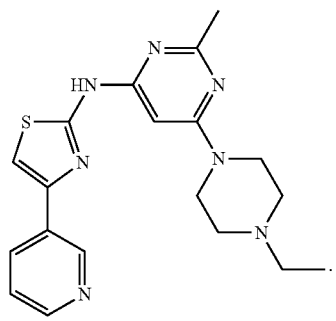 [SMILES: CCN1CCN(c2cc(Nc3nc(-c4cccnc4)cs3)nc(C)n2)CC1]
Listed below are exemplary compounds of this invention, each assigned a compound number.
1
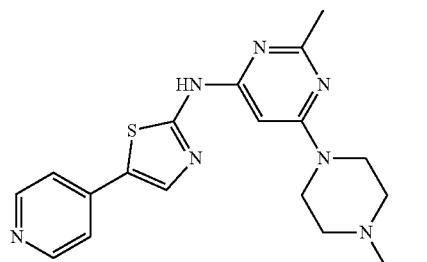
2
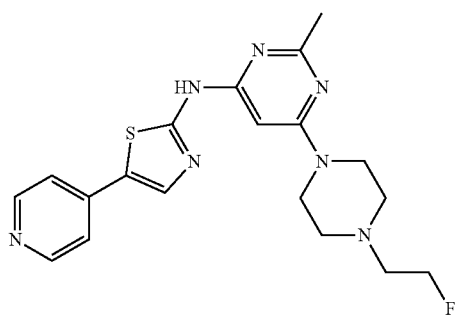
3
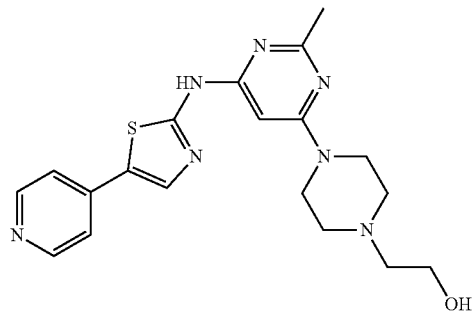
4
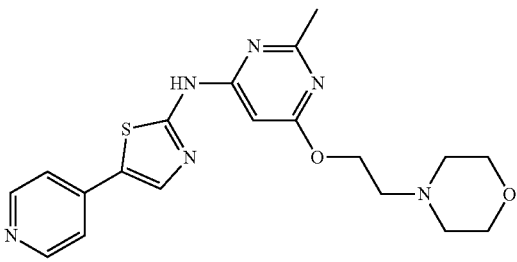
5
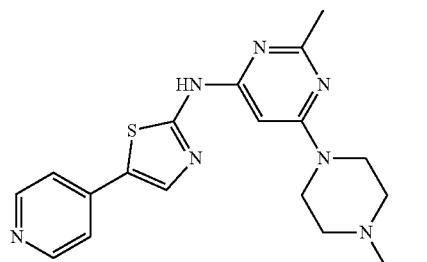
6
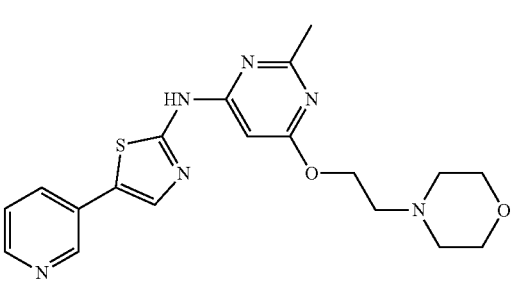
7
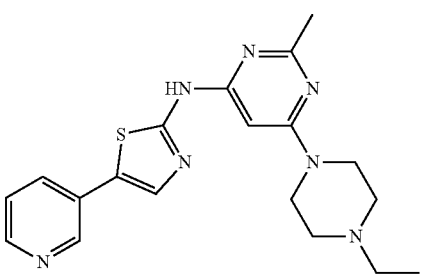

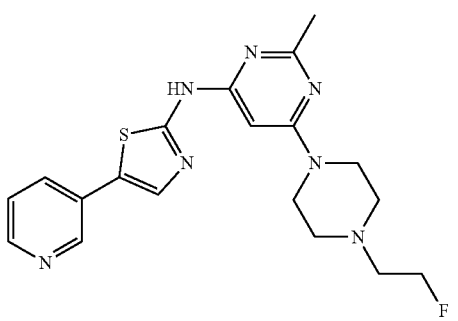

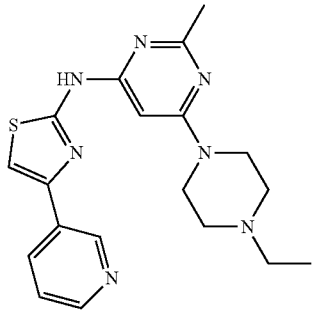

Also within this invention is a pharmaceutical composition containing one or more of the aminothiazole compounds of Formula (I) for treating cancer.

Further covered by this invention is a method for treating cancer, the method including administering to a subject in need thereof an effective amount of a compound of Formula (I).

Synthetic chemistry transformations and protecting group methodologies (protection and de-protection) used for synthesizing the compounds of Formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); and G. J. Yu et al., *J. Med. Chem.* 2008, 51, 6044-6054.

The compounds of Formula (I) thus prepared can be initially screened using biochemical assays, e.g., the kinase assays described in EXAMPLES 2-4 below, or cellular assays, e.g., the in vitro anticancer activity assay described in EXAMPLE 5 below, for their potency in inhibiting tyrosine kinases or inhibiting the growth of cancer cells expressing certain tyrosine kinases. They can be subsequently evaluated using in vivo assays, e.g., a xenograft animal model assay, for their activity in suppressing tumor growth in a mammal. The selected compounds can be further tested to verify their efficacy in treating cancer. For example, a compound can be administered to an animal (e.g., a mouse) having cancer and its therapeutic effect is then assessed. Based on the results, appropriate dosage ranges and administration routes can be investigated and determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

Shown in EXAMPLE 1 below are the synthesis and characterization of 13 exemplary compounds of Formula (I). The analytical data for the compounds thus prepared are also set forth in EXAMPLE 1 and the procedures for testing these compounds are described in EXAMPLES 2-5 that follow.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

EXAMPLE 1

Synthesis of Compounds 1-13

Compounds 1-13 were prepared according to the synthetic route shown in Scheme 1 below. Among the listed reagents, TEA is triethylamine, KOAc is potassium acetate, Pd(PPh$_3$)$_4$ is tetrakis(triphenylphosphine)palladium(0), DMAc is N,N-dimethylacetamide, CsF is cesium fluoride, HCl is hydrochloric acid, NaHCO$_3$ is sodium bicarbonate, NaH is sodium hydride, NMP is 1-methyl-2-pyrrolidinone, KOH potassium hydroxide, and DMSO is dimethyl sulfoxide.

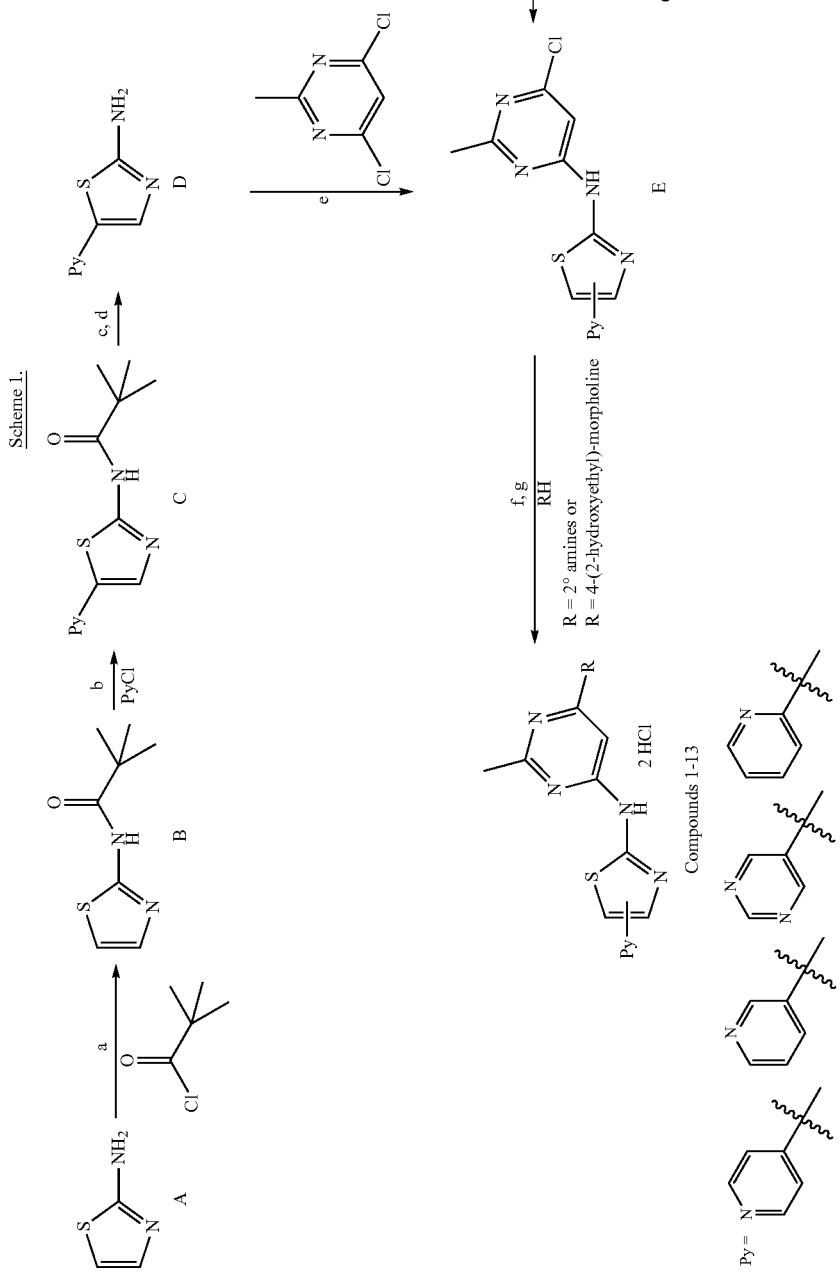

Step I. Synthesis of 2,2-dimethyl-N-thiazol-2-yl-propionamide B

To a mixture of 2-aminothiazole A (300 mmol) and triethylamine (330 mmol) in anhydrous $CH_2Cl_2$ (250 mL) at 0° C. was added trimethylacetyl chloride (310 mmol) and the mixture was stirred at room temperature under an argon atmosphere for 1 h. The mixture was washed with 6 N HCl (60 mL) and the organic layer was separated, dried over magnesium sulfate ($MgSO_4$), and concentrated under reduced pressure. The residue was purified by chromatography on silica gel (20% EtOAc/hexane) to give the titled product B as an off-white solid (72%). $^1$H NMR (300 MHz, DMSO-d6): δ 11.75 (s, 1H), 7.46 (d, J=6.0 Hz, 1H), 7.17 (d, J=6.0 Hz, 1H), 1.22 (s, 9H); MS ($ES^+$) m/z calcd. for $C_8H_{12}N_2OS$: 184.07; found: 185.1 ($M+H^+$).

Step II. Synthesis of Compound C (Py=pyridin-3-yl, pyridin-4-yl, and pyrimidin-5-yl)

A mixture of 2,2-dimethyl-N-thiazol-2-yl-propionamide B (30 mmol), chloropyridine (30 mmol), potassium acetate (120 mmol) and tetrakis(triphenylphosphine)palladium(0) (1.5 mmol) in N,N-dimethylacetamide (60 mL) was heated at 150° C. under an argon atmosphere for 24 h. Most of solvent was removed by distillation (120° C./160 mm Hg) and the residue was washed with water (250 mL). The precipitate was collected by filtration, redissolved in 10% $CH_3OH/CH_2Cl_2$ (200 mL) and filtered through a pad of Celite. The filtrate was concentrated under reduced pressure and purified by chromatography on silica gel (1% MeOH/ $CH_2Cl_2$) to give the desired product as an off-white solid (40-85%).

Step II. Synthesis of Compound C (Py=pyridin-2-yl)

A mixture of 2,2-dimethyl-N-thiazol-2-yl-propionamide B (10 mmol), chloropyridine (10 mmol), cesium fluoride (20 mmol) and tetrakis(triphenylphosphine)palladium(0) (0.5 mmol) in dimethyl sulfoxide (20 mL) was heated at 160° C. under an argon atmosphere for 16 h. The resultant mixture was partitioned with 0.5N HCl (150 mL) and $CH_2Cl_2$ (150 mL). The organic layer was separated, dried over $MgSO_4$, concentrated under reduced pressure and purified by chromatography on silica gel (3% acetone/$CH_2Cl_2$) to give the desired product as a pale brown solid (20%)

Only one of C was selected to show its NMR spectrum and Mass.

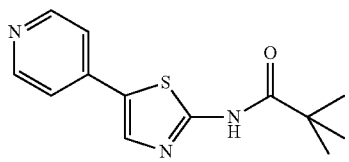 [SMILES: CC(C)(C)C(=O)Nc1ncc(-c2ccncc2)s1]

2,2-Dimethyl-N-(5-pyridin-4-yl-thiazol-2-yl)-propionamide. $^1$H NMR (400 MHz, $CDCl_3$): δ 9.28 (bs, 1H), 8.61 (dd, J=4.8, 1.6 Hz, 2H), 7.84 (s, 1H), 7.42 (dd, J=4.8, 1.6 Hz, 2H), 1.38 (s, 9H); MS ($ES^+$) m/z calcd. for $C_{13}H_{15}N_3OS$: 261.09; found: 262.1 ($M+H^+$).

Step III. Synthesis of Compound D

A mixture of C (5 mmol) and 12 N HCl (5 mL) in water (5 mL) was heated to reflux for 2 h. Most of solvent was removed under reduced pressure and the residue was diluted with $CH_3OH$ (15 mL). Most of solvent was removed by distillation and the residue was dried in vacuo to give D hydrochloride as a pale brown solid.

To a stirred suspension of the above solid in water (30 mL) at room temperature was adjusted to pH=7 with sodium bicarbonate and the mixture was stirred at 50° C. for 2 h. The precipitate was collected by filtration and dried in vacuo to give the desired product D as a pale brown solid (85-90%).

Only one of D was selected to show its NMR spectrum and Mass.

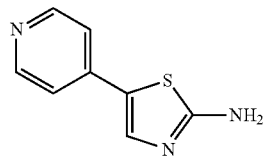 [SMILES: Nc1ncc(-c2ccncc2)s1]

5-Pyridin-4-yl-thiazol-2-ylamine. $^1$H NMR (300 MHz, DMSO-d6): δ 8.41 (dd, J=4.8, 1.5 Hz, 2H), 7.73 (s, 1H), 7.48 (s, 2H), 7.35 (dd, J=4.8, 1.5 Hz, 2H); MS ($ES^+$) m/z calcd. for $C_8H_7N_3S$: 177.04; found: 178.1 ($M+H^+$).

Step IV. Synthesis of Compound E

To a mixture of D or commercially available 4-pyridin-3-yl-thiazol-2-ylamine (4 mmol) and 4,6-dichloro-2-methylpyrimidine (8 mmol) in 1-methyl-2-pyrrolidinone (20 mL) at 0° C. was added sodium hydride (60% in oil, 10 mmol) and the mixture was stirred at 0° C. under an argon atmosphere for 1 h. The reaction was quenched with water (100 mL) at 0° C. and was adjusted to pH=2 with 6 N HCl. The slurry was adjusted to pH=7 with sodium bicarbonate and the precipitate was collected by filtration, washed with water (50 mL) and dried in vacuo. The residue was purified by chromatography on silica gel (20% EtOAc/$CH_2Cl_2$, then 5% to 10% MeOH/$CH_2Cl_2$ gradient) to give the desired product E as a brown solid (45-60%).

Only one of E was selected to show its NMR spectrum and Mass.

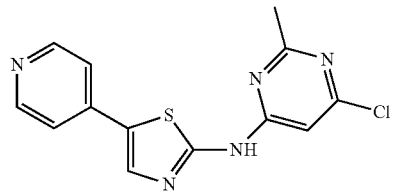 [SMILES: Cc1nc(Cl)cc(Nc2ncc(-c3ccncc3)s2)n1]

(6-Chloro-2-methyl-pyrimidin-4-yl)-(5-pyridin-4-yl-thiazol-2-yl)-amine. $^1$H NMR (300 MHz, DMSO-d6): δ 12.15 (s, 1H), 8.53 (dd, J=4.5, 1.5 Hz, 2H), 8.18 (s, 1H), 7.59 (dd, J=4.5, 1.5 Hz, 2H), 6.90 (s, 1H), 2.59 (s, 3H); MS ($ES^+$) m/z calcd. for $C_{13}H_{10}ClN_5S$: 303.03; found: 304.1 ($M+H^+$).

Step V. Synthesis of Compounds 1-4 and 7-13

A mixture of Compound E (2 mmol) and 1-ethylpiperazine (8 mmol) in dimethyl sulfoxide (2 mL) was heated at 100° C. for 1 h. After cooling to room temperature, the mixture was diluted with water (50 mL). The precipitate was collected by filtration, washed with water (10 mL) and dried in vacuo. The residue was purified by chromatography on aluminium oxide (0.5% to 1.5% MeOH/CH$_2$Cl$_2$ gradient) to give freebase of each Compounds 1-4 and 7-13 as an off-white solid.

To a stirred 6 N HCl (10 mL) at 0° C. was added the above solid and the solution was filtered through a 0.45 μm PVDF membrane. To the stirred filtrate was added acetone (40 mL) dropwise over the course of 1 h and was stirred for an additional 1 h at 0° C. The precipitate was collected by filtration, washed with acetone (15 mL) and dried in vacuo to give the HCl salt of each Compounds 1-4 and 7-13 as a yellow solid (90-95%).

[6-(4-Ethyl-piperazin-1-yl)-2-methyl-pyrimidin-4-yl]-(5-pyridin-4-yl-thiazol-2-yl)-amine hydrochloride salt (Compound 1). $^1$H NMR (400 MHz, DMSO-d6): δ 11.55 (bs, 1H), 8.72 (d, J=5.6 Hz, 2H), 8.61 (s, 1H), 8.14 (d, J=5.2 Hz, 2H), 6.27 (s, 1H), 4.35 (d, J=13.2 Hz, 2H), 3.55 (d, J=12.0 Hz, 2H), 3.45 (t, J=13.0 Hz, 2H), 3.13 (t, J=5.8 Hz, 2H), 3.02 (q, J=10.0 Hz, 2H), 2.50 (s, 3H), 1.28 (t, J=6.8 Hz, 3H); MS (ES$^+$) m/z calcd. for C$_{19}$H$_{23}$N$_7$S: 381.17; found: 382.2 (M+H$^+$).

{6-[4-(2-Fluoro-ethyl)-piperazin-1-yl]-2-methyl-pyrimidin-4-yl}-(5-pyridin-4-yl-thiazol-2-yl)-amine hydrochloride salt (Compound 2). $^1$H NMR (300 MHz, DMSO-d6): δ 11.89 (bs, 1H), 8.73 (d, J=6.3 Hz, 2H), 8.62 (s, 1H), 8.15 (d, J=5.7 Hz, 2H), 6.26 (s, 1H), 4.95 (d, J=47.4 Hz, 2H), 4.38 (s, 2H, overlapping with water peak), 3.70-3.35 (m, 6H), 3.18 (bs, 2H), 2.50 (s, 3H); MS (ES$^+$) m/z calcd. for C$_{19}$H$_{22}$FN$_7$S: 399.16; found: 400.1 (M+H$^+$).

2-{4-[2-Methyl-6-(5-pyridin-4-yl-thiazol-2-ylamino)-pyrimidin-4-yl]-piperazin-1-yl}-ethanol hydrochloride salt (Compound 3). $^1$H NMR (400 MHz, DMSO-d6): δ 11.03 (s, 1H), 8.73 (d, J=7.2 Hz, 2H), 8.63 (s, 1H), 8.15 (d, J=7.2 Hz, 2H), 6.26 (s, 1H), 4.34 (d, J=12.4 Hz, 2H), 3.82 (t, J=5.2 Hz, 2H), 3.62 (d, J=12.0 Hz, 2H), 3.43 (t, J=12.4 Hz, 2H), 3.30-3.09 (m, 4H), 2.49 (s, 3H); MS (ES$^+$) m/z calcd. for C$_{19}$H$_{23}$N$_7$OS: 397.17; found: 398.1 (M+H$^+$).

[6-(4-Dimethylamino-piperidin-1-yl)-2-methyl-pyrimidin-4-yl]-(5-pyridin-4-yl-thiazol-2-yl)-amine hydrochloride salt (Compound 4). $^1$H NMR (300 MHz, DMSO-d6): δ 11.07 (s, 1H), 8.73 (d, J=6.9 Hz, 2H), 8.62 (s, 1H), 8.15 (d, J=6.9 Hz, 2H), 6.25 (s, 1H), 4.43 (d, J=12.9 Hz, 2H), 3.44 (quin, J=5.2 Hz, 1H), 2.94 (t, J=12.5 Hz, 2H), 2.69 (d, J=4.5 Hz, 6H), 2.49 (s, 3H), 2.15 (d, J=10.5 Hz, 2H), 1.60 (q, J=11.0 Hz, 2H); MS (ES$^+$) m/z calcd. for C$_{20}$H$_{25}$N$_7$S: 395.19; found: 396.1 (M+H$^+$).

[6-(4-Ethyl-piperazin-1-yl)-2-methyl-pyrimidin-4-yl]-(5-pyridin-3-yl-thiazol-2-yl)-amine hydrochloride salt (Compound 7). $^1$H NMR (400 MHz, DMSO-d6): δ 11.23 (bs, 1H), 9.15 (s, 1H), 8.68 (d, J=5.2 Hz, 1H), 8.60 (d, J=8.0 Hz, 1H), 8.19 (s, 1H), 7.93 (t, J=6.2 Hz, 1H), 6.21 (s, 1H), 4.35 (d, J=14.4 Hz, 2H), 3.55 (d, J=11.6 Hz, 2H), 3.40 (t, J=13.2 Hz, 2H), 3.13 (t, J=5.8 Hz, 2H), 3.01 (q, J=6.9 Hz, 2H), 2.50 (s, 3H), 1.28 (t, J=6.6 Hz, 3H); MS (ES$^+$) m/z calcd. for C$_{19}$H$_{23}$N$_7$S: 381.17; found: 382.2 (M+H$^+$).

{6-[4-(2-Fluoro-ethyl)-piperazin-1-yl]-2-methyl-pyrimidin-4-yl}-(5-pyridin-3-yl-thiazol-2-yl)-amine hydrochloride salt (Compound 8). $^1$H NMR (400 MHz, DMSO-d6): δ 11.80 (bs, 1H), 9.16 (s, 1H), 8.68 (d, J=5.6 Hz, 1H), 8.62 (d, J=8.0 Hz, 1H), 8.20 (s, 1H), 7.95 (t, J=6.8 Hz, 1H), 6.22 (s, 1H), 4.98 (d, J=46.8 Hz, 2H), 4.34 (bs, 2H), 3.70-3.35 (m, 6H), 3.16 (bs, 2H), 2.49 (s, 3H); MS (ES$^+$) m/z calcd. for C$_{19}$H$_{22}$FN$_7$S: 399.16; found: 400.1 (M+H$^+$).

2-{4-[2-Methyl-6-(5-pyridin-3-yl-thiazol-2-ylamino)-pyrimidin-4-yl]-piperazin-1-yl}-ethanol hydrochloride salt (Compound 9). $^1$H NMR (400 MHz, DMSO-d6): δ 11.02 (bs, 1H), 9.18 (s, 1H), 8.69 (s, 1H), 8.64 (d, J=7.6 Hz, 1H), 8.22 (s, 1H), 7.96 (d, J=5.2 Hz, 1H), 6.25 (s, 1H), 4.33 (d, J=11.2 Hz, 2H), 3.80 (s, 1H), 3.60 (d, J=11.6 Hz, 2H), 3.19 (s, 2H), 3.13 (s, 2H), 2.48 (s, 3H); MS (ES$^+$) m/z calcd. for C$_{19}$H$_{23}$N$_7$OS: 397.17; found: 398.1 (M+H$^+$).

[6-(4-Dimethylamino-piperidin-1-yl)-2-methyl-pyrimidin-4-yl]-(5-pyridin-3-yl-thiazol-2-yl)-amine hydrochloride salt (Compound 10). $^1$H NMR (400 MHz, DMSO-d6): δ 11.27 (bs, 1H), 9.18 (s, 1H), 8.69 (d, J=5.2 Hz, 1H), 8.64 (d, J=8.0 Hz, 1H), 8.23 (s, 1H), 7.97 (t, J=6.8 Hz, 1H), 6.36 (bs, 1H), 4.42 (d, J=8.8 Hz, 2H), 3.43 (bs, 1H), 2.99 (t, J=12.4 Hz, 2H), 2.68 (s, 3H), 2.67 (s, 3H), 2.55 (s, 3H), 2.17 (d, J=10.8 Hz, 2H), 1.64 (q, J=9.2 Hz, 2H); MS (ES$^+$) m/z calcd. for C$_{20}$H$_{25}$N$_7$S: 395.19; found: 396.2 (M+H$^+$).

[6-(4-Ethyl-piperazin-1-yl)-2-methyl-pyrimidin-4-yl]-(5-pyridin-2-yl-thiazol-2-yl)-amine hydrochloride salt (Compound 11). $^1$H NMR (300 MHz, DMSO-d6): δ 11.34 (s, 1H), 8.54 (d, J=4.8 Hz, 1H), 8.32 (s, 1H), 8.01-7.96 (m, 2H), 7.40-7.34 (m, 1H), 6.31 (s, 1H), 4.37 (d, J=13.2 Hz, 2H), 3.62-3.38 (m, 4H), 3.20-2.90 (m, 4H), 2.47 (s, 3H), 1.26 (t, J=7.4 Hz, 3H); MS (ES$^+$) m/z calcd. for C$_{19}$H$_{23}$N$_7$S: 381.17; found: 382.2 (M+H$^+$).

[6-(4-Ethyl-piperazin-1-yl)-2-methyl-pyrimidin-4-yl]-(5-pyrimidin-5-yl-thiazol-2-yl)-amine hydrochloride salt (Compound 12). $^1$H NMR (400 MHz, DMSO-d6): δ 11.35 (bs, 1H), 9.20-9.03 (m, 3H), 8.09 (s, 1H), 6.28 (s, 1H), 4.40 (s, 2H), 3.56 (d, J=12.4 Hz, 2H), 3.44 (d, J=7.4 Hz, 2H), 3.13 (bs, 2H), 3.02 (d, J=8.0 Hz, 2H), 1.28 (bs, 3H); MS (ES$^+$) m/z calcd. for C$_{18}$H$_{22}$N$_8$S: 382.17; found: 383.3 (M+H$^+$).

[6-(4-Ethyl-piperazin-1-yl)-2-methyl-pyrimidin-4-yl]-(4-pyridin-3-yl-thiazol-2-yl)-amine hydrochloride salt (Compound 13). $^1$H NMR (400 MHz, DMSO-d6): δ 11.80 (bs, 1H), 11.54 (bs, 1H), 9.28 (s, 1H), 8.94 (d, J=8.4 Hz, 1H), 8.84 (d, J=5.2 Hz, 1H), 8.15-8.07 (m, 2H), 6.31 (bs, 2H), 4.35 (d, J=14.0 Hz, 2H), 3.55 (d, J=12.0 Hz, 2H), 3.45 (t, J=13.0 Hz, 2H), 3.15-3.07 (m, 2H), 3.00 (q, J=10.0 Hz, 2H), 2.49 (s, 3H), 1.27 (t, J=7.4 Hz, 3H); MS (ES$^+$) m/z calcd. for C$_{19}$H$_{23}$N$_7$S: 381.17; found: 382.1 (M+H$^+$).

Step V. Synthesis of Compounds 5 and 6

To a mixture of Compound E (1 mmol) and 4-(2-hydroxyethyl)-morpholine (4 mmol) in diglyme (1 mL) at 100° C. was added potassium hydroxide (10 mmol) and the mixture was stirred at 160° C. under an argon atmosphere for 10 min. The reaction was quenched with water (20 mL) at 0° C. and was adjusted to pH=2 with 6 N HCl. The slurry was adjusted to pH=7 with sodium bicarbonate and the precipitate was collected by filtration, washed with water (10 mL) and dried in vacuo. The residue was purified by chromatography on aluminium oxide (0.5% to 1.5% MeOH/CH$_2$Cl$_2$ gradient) to give freebase of Compound 6 as an off-white solid.

To a suspension of the above solid in MeOH (10 mL) at 0° C. was added 6 N HCl (1 mL) with stirring. Most of solvent was removed under reduced pressure and the residue was treated with EtOH (10 mL). The precipitate was collected by filtration, washed with acetone (10 mL) and dried in vacuo to give the HCl salt of each compounds 5-6 as a yellow solid (45-50%).

[2-Methyl-6-(2-morpholin-4-yl-ethoxy)-pyrimidin-4-yl]-(5-pyridin-4-yl-thiazol-2-yl)-amine hydrochloride salt (Compound 5). $^1$H NMR (400 MHz, DMSO-d6): δ 11.61 (s, 1H), 8.74 (d, J=5.2 Hz, 2H), 8.64 (s, 1H), 8.17 (d, J=5.2 Hz, 2H), 6.37 (s, 1H), 4.72 (s, 2H), 4.00-3.80 (m, 4H), 3.64-3.42 (m, 4H), 3.16 (bs, 2H), 2.59 (s, 3H); MS (ES$^+$) m/z calcd. for C$_{19}$H$_{22}$N$_6$O$_2$S: 398.15; found: 399.2 (M+H$^+$).

[2-Methyl-6-(2-morpholin-4-yl-ethoxy)-pyrimidin-4-yl]-(5-pyridin-3-yl-thiazol-2-yl)-amine hydrochloride salt (Compound 6). $^1$H NMR (400 MHz, DMSO-d6): δ 11.51

(bs, 1H), 9.20 (s, 1H), 8.71 (d, J=5.6 Hz, 1H), 8.66 (d, J=8.4 Hz, 1H), 8.24 (s, 1H), 7.98 (dd, J=8.0, 5.6 Hz, 1H), 6.35 (s, 1H), 4.72 (t, J=4.8 Hz, 2H), 3.96 (d, J=10.8 Hz, 2H), 3.85 (t, J=12.0 Hz, 2H), 3.55 (bs, 2H), 3.47 (d, J=12.4 Hz, 2H), 3.19 (bs, 2H), 2.59 (s, 3H); MS (ES$^+$) m/z calcd. for $C_{19}H_{22}N_6O_2S$: 398.15; found: 399.1 (M+H$^+$).

EXAMPLE 2

Inhibiting FLT3 Activity

A study was carried out as follows to test certain compounds prepared according to EXAMPLE 1 in inhibiting FLT3 activity.

GST-FLT3-KD$^{WT}$ containing the FLT3 kinase catalytic domain (residues Y567-5993) was expressed in Sf9 insect cells transfected the baculovirus containing pBac-PAK8-GST-FLT3-KD plasmid. An FLT3$^{WT}$ Kinase-Glo assay was carried out in 96-well plates at 30° C. for 4 hrs to test compound in a final volume of 50 µl including the following components: 75 ng GST-FLT3-KD$^{WT}$ proteins, 25 mM HEPES, pH 7.4, 4 mM MnCl$_2$, 10 mM MgCl$_2$, 2 mM DTT, 0.02% Triton X-100, 0.1 mg/ml bovine serum albumin, 25 µl M Her2 peptide substrate, 0.5 mM Na$_3$VO$_4$, and 1 µM ATP. Following incubation, 50 µl Kinase-Glo Plus Reagent (Promega, Madison, Wis., USA) was added to each well and the mixture was incubated at 25° C. for 20 min. A 70-µL aliquot of each reaction mixture was transferred to a black microtiter plate and the luminescence was measured on Wallac Vector 1420 multilabel counter (PerkinElmer, Shelton, Conn., USA).

Multiple compounds were tested. Unexpectedly, Compounds 1-11 showed IC$_{50}$ (the concentration of an inhibitor where the response is reduced by half) values lower than 100 nM.

EXAMPLE 3

Inhibiting VEGFR2 Activity

A study was carried out as follows to test certain compounds prepared according to EXAMPLE 1 in inhibiting VEGFR2 activity. Note that VEGFR2 is one of the three main subtypes of VEGFR.

The recombinant GST-VEGFR2 (residues V789-V1356) containing kinase domain was expressed in Sf9 insect cells. The kinase assay was carried out in 96-well plates with tested compound in a final volume of 50 µl reaction at 30° C. for 120 minutes with following components: 25 mM HEPES pH 7.4, 10 mM MgCl$_2$, 4 mM MnCl$_2$, 0.5 mM Na3VO4, 2 mM DTT, 0.02% Triton X100, 0.01% BSA, 1 µM ATP, 2 µM polyGlu4:Tyr peptide, 50~100 ng recombinant VEGFR2. Following incubation, 50 µl Kinase-Glo Plus Reagent (Promega, Madison, Wis., USA) was added to each well and the mixture was incubated at 25° C. for 20 min. A 70-µL aliquot of each reaction mixture was transferred to a black microtiter plate and the luminescence was measured on Wallac Vector 1420 multilabel counter (PerkinElmer, Shelton, Conn., USA).

Multiple compounds were tested in the VEGFR2 assay. Compounds 1, 9 and 10 unexpectedly showed IC$_{50}$ values lower than 30 nM.

EXAMPLE 4

Inhibiting c-Kit Activity

A study was carried out as follows to test certain compounds prepared according to EXAMPLE 1 in inhibiting c-Kit activity.

The N-terminal His-tagged human c-KIT (residues T544-V976) recombinant proteins, expressed in Sf9 baculovirus-insect cell expression systems, were purified for c-KIT ADP Kinase-Glo assay. A c-Kit-ADP Kinase-Glo assay was carried out in 96-well plates at 30° C. for 150 mins with a final volume of 10 µl, including 40 mM Tris pH 7.4, 20 mM MgCl$_2$, 2 mM MnCl$_2$, 2 mM DTT, 0.01% BSA, 20 µM ATP, 20 µM poly(Glu,Tyr) 4:1 peptide, 0.1 mM Na$_3$VO$_4$, 250 ng of recombinant c-Kit proteins, and a tested compound at the indicated concentration. The reactions were stopped by the addition of 5 µl ADP-Glo™ Reagent (Promega, Madison, Wis., USA) at 25° C. with 40 min incubation, followed by 10 µl of kinase detection reagent for a further 30 min. Finally, a 30 µl aliquot of each reaction mixture was transferred to a black microtiter plate and the luminescence was measured on Wallac Vector 1420 multilabel counter (Perkin-Elmer, Shelton, Conn., USA).

Multiple compounds were tested. Unexpectedly, Compounds 1-7 and 11-12 showed IC$_{50}$ values lower than 100 nM.

EXAMPLE 5

In Vitro Anticancer Activity

A study was carried out as follows to evaluate in vitro anticancer activity of certain compounds prepared according to EXAMPLE 1 using cell lines and MTS cell viability assays (MTS represents 3-(4,5-dimethylthiazol-2-yl)-5-(3-carboxymethoxyphenyl)-2-(4-sulfophenyl)-2H-tetrazolium).

Leukemia cell lines MOLM-13, MV4:11, and Kasumin-1 were purchased from American Type Culture Collection (ATCC, Manassas, Va., USA). The human gastrointestinal stromal tumor GIST-T1 cell line was purchased from Cosmo Bio Co., LTD (Tokyo, Japan). All leukemia cell lines were maintained in RPMI 1640 medium supplemented with 10% fetal bovine serum (FBS), 10 U/ml penicillin, and 10 g/ml streptomycin at 37° C. and 5% CO$_2$. The cell line GIST-T1 was cultured in DMEM medium supplemented with 10% FBS, 0.01% nonessential amino acids, 10 U/ml penicillin, and 10 g/ml streptomycin.

GIST882, GIST48 and GIST430 cells were all cultured in incubators maintained at 37° C. and 5% CO$_2$. GIST882 was cultured in RPMI-1640 supplemented with 20% fetal bovine serum (FBS). GIST48 was cultured with F10 supplemented with 20% FBS, 0.5% Mito, serum extender (BD Bioscience, 355006) and 1% pituitary extract bovine (BD Bioscience 354123). GIST430 was cultured in IMDM supplemented with 20% FBS. GIST882, GIST430 and GIST48 cells were provided by Dr. Jonathan A. Fletcher (Harvard Medical School, US).

MOLM-13, MV4:11, and Kasumin-1 MTS Assays

Cells were seeded in 96-well culture plates at a density of 1×10$^4$ cells/100 µl/well in triplicates and were treated for 72 hours with an indicated concentration of test compound ranging from 1 nM to 10 µM. Colorimetric CellTiter 96® Aqueous One Solution Cell Proliferation assay (MTS assay; Promega, Madison, Wis., USA) was used to determine the cytotoxicity. The optical density at 492 nm was measured using a microplate photometer (Victor2; Perkin-Elmer, Waltham, Mass., USA). IC$_{50}$ values were determined by MTS assay when cells were treated with test compound for 72 hours and calculated with GraphPad Prism 6. Each experiment was in triplicate.

GIST-T1 MTS Assay

GIST-T1 cells were seeded in 96-well culture plates at a density of 8000 cells/100 μl/well in triplicates and were treated for 72 hours with an indicated concentration of test compound ranging from 1 nM to 10 μM. Colorimetric CellTiter 96® Aqueous One Solution Cell Proliferation assay (MTS assay; Promega, Madison, Wis., USA) was used to determine the cytotoxicity. The optical density at 492 nm was measured using a microplate photometer (Victor2; Perkin-Elmer, Waltham, Mass., USA). $IC_{50}$ values were determined by MTS assay when cells were treated with test compound for 72 hours and calculated with GraphPad Prism 6. Each experiment was in triplicate.

GIST882, GIST48, and GIST430 MTS Assays

GIST cells ($4 \times 10^4$) were treated with different dosage of compounds. The treated GIST882 cells were incubated for 144 hours and GIST48 and GIST430 cells were incubated for 120 hours at 37° C. in 5% $CO_2$. Cell proliferation was determined by incubating the cells with methylene blue (Clontech, Calif., US) for 1 hour. The absorbance was measured at 450 nm using SpectraMax M5 microplate reader (Molecular Devices, US).

The $GI_{50}$ (the concentration for 50% of maximal inhibition of cell proliferation) values of certain compounds of Formula (I) are shown in the table below:

| | $GI_{50}$ (nM) | | | | | | |
|---|---|---|---|---|---|---|---|
| Compound | MOLM-13 | MV4:11 | Kasumi-1 | GIST-T1 | GIST430 | GIST48 | GIST882 |
| 1 | 10 | 13 | 11 | 11 | 3.8 | 19 | 5.0 |
| 7 | 62 | 34 | 266 | 53 | 60 | 820 | 20 |
| 12 | 211 | 132 | 349 | 119 | ND | ND | ND |

ND, not determined.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I) below or a pharmaceutically acceptable salt thereof:

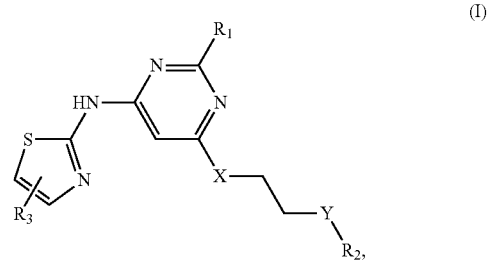

(I)

wherein
$R_1$ is $C_{1-6}$ alkyl or $C_{1-6}$ thioalkyl;
X is O or $NR_a$, in which $R_a$ is H or $C_{1-6}$ alkyl;
Y is $CR_bR_c$ or $NR_d$, in which each of $R_b$ and $R_c$, independently, is H, halo, $C_{1-6}$ alkyl, $C_{1-6}$ alkoxyl, or amino, or $R_b$, together with $R_a$, the carbon atom bonded to $R_b$, and the nitrogen atom bonded to $R_a$, is $C_{3-10}$ heterocycloalkyl; and $R_d$ is H or $C_{1-6}$ alkyl, or $R_d$, together with $R_a$ and the nitrogen atoms bonded to $R_d$ and $R_a$, is $C_{3-10}$ heterocycloalkyl;
$R_2$ is —$CH_2CH_2R_e$ or $NR_fR_g$, in which $R_e$ is H, halo, $C_{1-6}$ alkyl, or $OR_h$ and each of $R_f$ and $R_g$, independently, is $C_{1-6}$ alkyl or $C_{3-8}$ cycloalkyl, $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; and
$R_3$ is 6-membered heteroaryl.

2. The compound or salt of claim 1, wherein the compound is of formula (II):

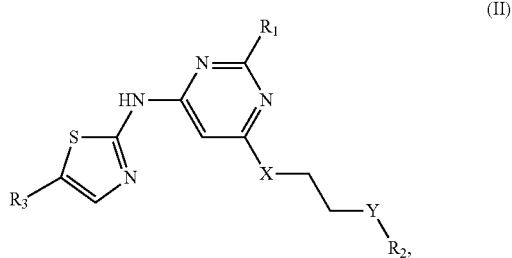

(II)

in which $R_1$ is $C_{1-6}$ alkyl.

3. The compound or salt of claim 2, wherein X is O, Y is $NR_d$, and $R_2$ is —$CH_2CH_2R_e$, in which $R_e$ is $OR_h$, $R_h$, together with $R_d$, the oxygen atom bonded to $R_h$, and the nitrogen atom bonded to $R_d$, being $C_{3-10}$ heterocycloalkyl.

4. The compound or salt of claim 2, wherein X is $NR_a$ and Y is $CR_bR_c$ or $NR_d$, in which $R_a$, together with $R_b$, the nitrogen atom bonded to $R_a$, and the carbon atom bonded to $R_b$, is $C_{3-10}$ heterocycloalkyl; $R_c$ is H, halo, $C_{1-6}$ alkyl, $C_{1-6}$ alkoxyl, or amino; and $R_d$, together with $R_a$ and the nitrogen atoms bonded to $R_a$ and $R_d$, is $C_{3-10}$ heterocycloalkyl.

5. The compound or salt of claim 4, wherein X is $NR_a$, Y is $CR_bR_c$, and $R_2$ is $NR_fR_g$, in which $R_a$, together with $R_b$, the nitrogen atom bonded to $R_a$, and the carbon atom bonded to $R_b$, is $C_{3-10}$ heterocycloalkyl; $R_c$ is H, halo, $C_{1-6}$ alkyl, $C_{1-6}$ alkoxyl, or amino; and each of $R_f$ and $R_g$ is $C_{1-6}$ alkyl.

6. The compound or salt of claim 4, wherein X is $NR_a$, Y is $NR_d$, and $R_2$ is $-CH_2CH_2R_e$, in which $R_a$, together with $R_d$ and the nitrogen atoms bonded to $R_a$ and $R_d$, is $C_{3-10}$ heterocycloalkyl; and $R_e$ is H, halo, or $OR_h$, $R_h$ being H or $C_{1-6}$ alkyl.

7. The compound or salt of claim 1, wherein $R_3$ is 6-membered heteroaryl substituted with one or more $(CH_2)_n$Z moieties independently, in which n is 0 or 1 and Z is H, halo, CN, OH, $CF_3$, $C_{1-6}$ alkyl, or $C_{1-6}$ alkoxyl; or is 6-membered heteroaryl fused with a phenyl ring substituted with one or more substituents independently selected from the group consisting of H, halo, CN, OH, $CF_3$, $C_{1-6}$ alkyl, and $C_{1-6}$ alkoxyl.

8. The compound or salt of claim 7, wherein $R_3$ is 6-membered heteroaryl substituted with one or more $(CH_2)_n$Z moieties independently, in which n is 0 or 1 and Z is H, halo, CN, OH, $CF_3$, $C_{1-6}$ alkyl, or $C_{1-6}$ alkoxyl.

9. The compound or salt of claim 8, wherein $R_3$ is pyridyl or pyrimidyl.

10. The compound or salt of claim 3, wherein $R_3$ is 6-membered heteroaryl substituted with one or more $(CH_2)_n$Z moieties independently, in which n is 0 or 1 and Z is H, halo, CN, OH, $CF_3$, $C_{1-6}$ alkyl, or $C_{1-6}$ alkoxyl; or is 6-membered heteroaryl fused with a phenyl ring substituted with one or more substituents independently selected from the group consisting of H, halo, CN, OH, $CF_3$, $C_{1-6}$ alkyl, and $C_{1-6}$ alkoxyl.

11. The compound or salt of claim 10, wherein $R_3$ is pyridyl or pyrimidyl.

12. The compound or salt of claim 11, wherein the compound is

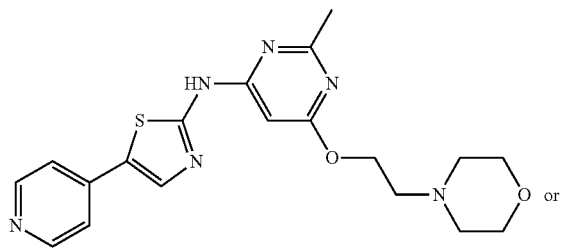
or

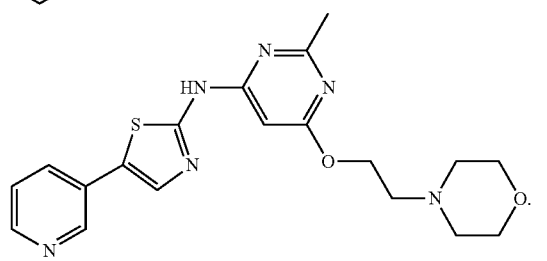

13. The compound or salt of claim 5, wherein $R_3$ is 6-membered heteroaryl substituted with one or more $(CH_2)_n$Z moieties independently, in which n is 0 or 1 and Z is H, halo, CN, OH, $CF_3$, $C_{1-6}$ alkyl, or $C_{1-6}$ alkoxyl; or is 6-membered heteroaryl fused with a phenyl ring substituted with one or more substituents independently selected from the group consisting of H, halo, CN, OH, $CF_3$, $C_{1-6}$ alkyl, and $C_{1-6}$ alkoxyl.

14. The compound or salt of claim 13, wherein $R_3$ is pyridyl or pyrimidyl.

15. The compound or salt of claim 14, wherein the compound is

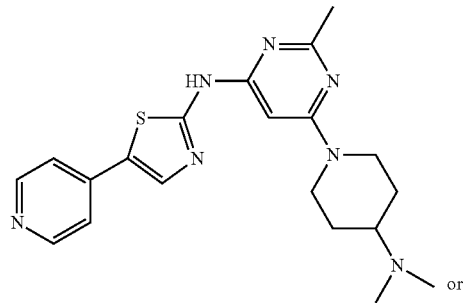
or

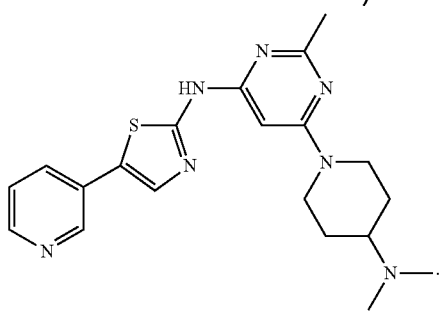

16. The compound or salt of claim 6, wherein $R_3$ is 6-membered heteroaryl substituted with one or more $(CH_2)_n$Z moieties independently, in which n is 0 or 1 and Z is H, halo, CN, OH, $CF_3$, $C_{1-6}$ alkyl, or $C_{1-6}$ alkoxyl; or is 6-membered heteroaryl fused with a phenyl ring substituted with one or more substituents independently selected from the group consisting of H, halo, CN, OH, $CF_3$, $C_{1-6}$ alkyl, and $C_{1-6}$ alkoxyl.

17. The compound or salt of claim 16, wherein $R_3$ is pyridyl or pyrimidyl.

18. The compound or salt of claim 17, wherein the compound is one of the following compounds:

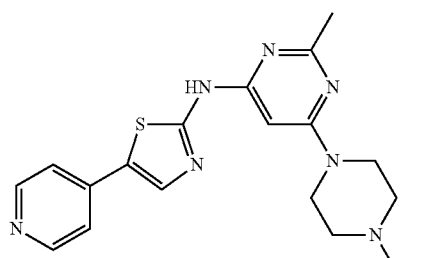

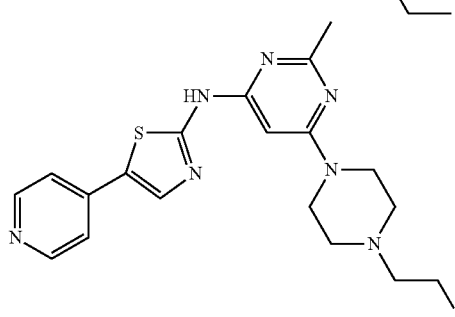

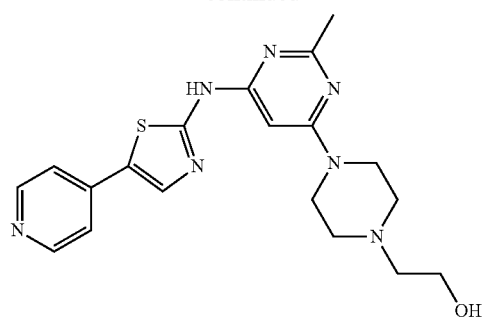
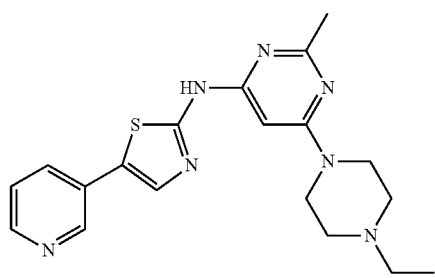
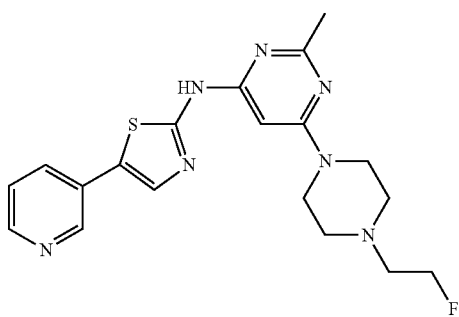
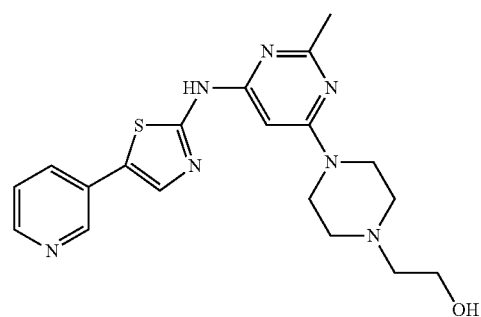
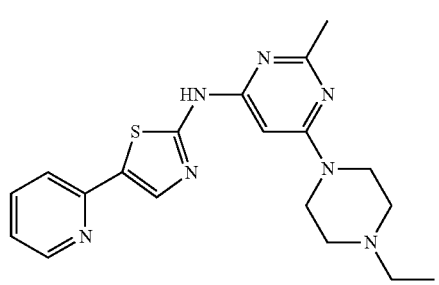
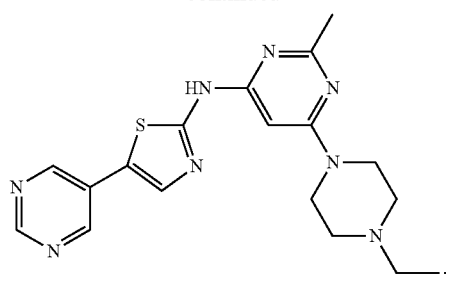
19. The compound or salt of claim 1, wherein the compound is one of the following compounds:
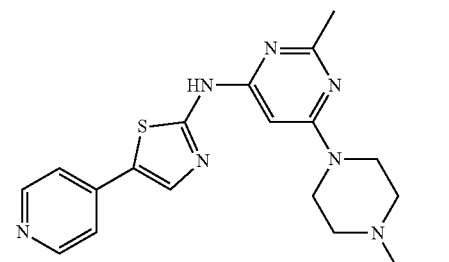
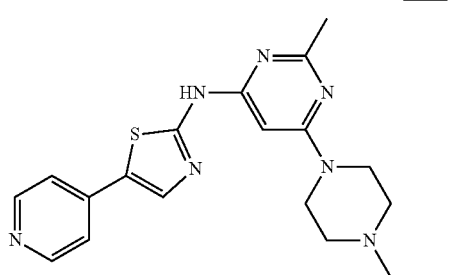
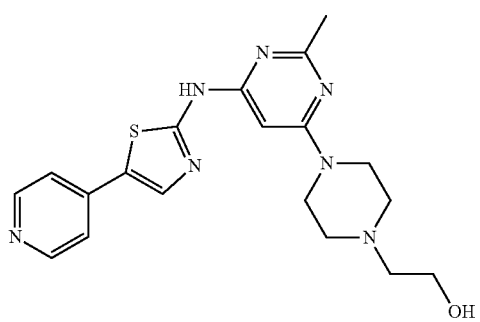
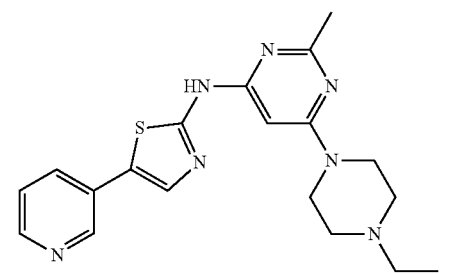

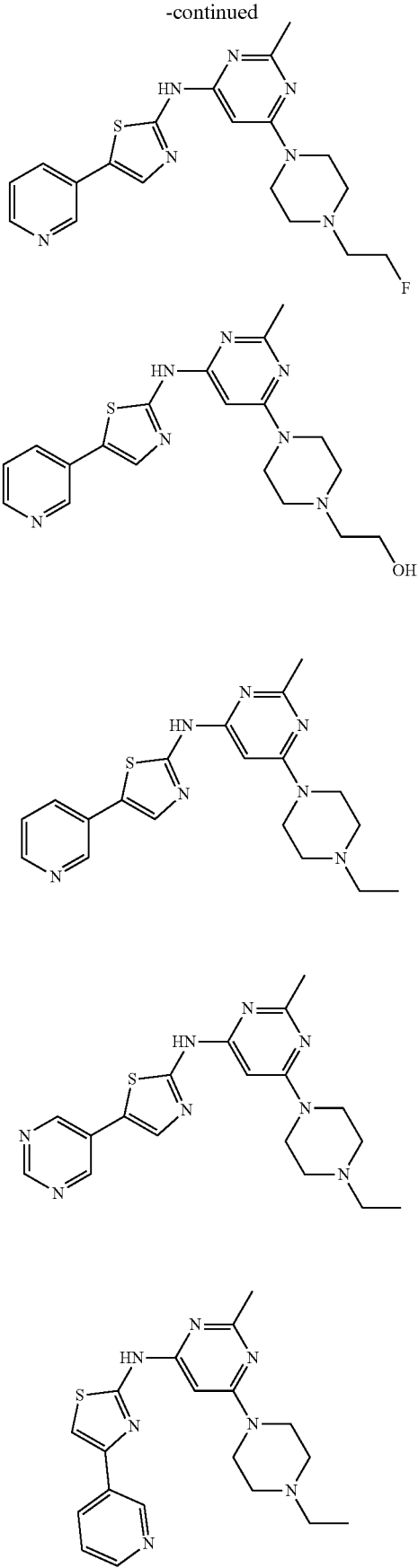
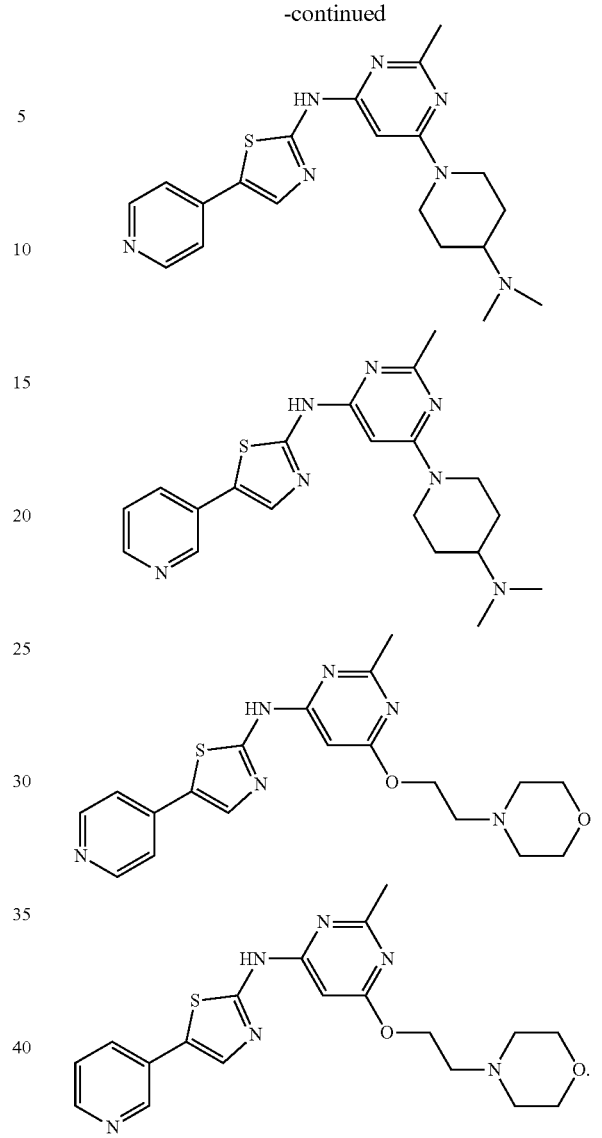
20. The compound or salt of claim 1, wherein the compound is of formula (III):
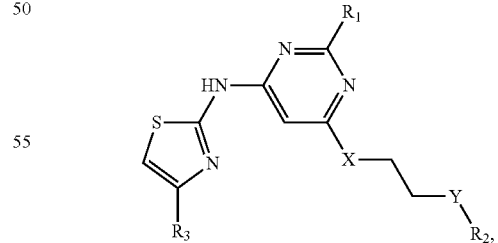
in which $R_1$ is $C_{1-6}$ alkyl.
21. A pharmaceutical composition comprising a pharmaceutically acceptable carrier and a compound or salt of claim 1.
22. A method of inhibiting a tyrosine kinase, comprising contacting the tyrosine kinase with an effective amount of a compound or salt of claim 1.

23. A method of treating cancer associated with a tyrosine kinase, the method comprising administering to a subject having said cancer an effective amount of a compound or salt of claim 1.

24. The method of claim 23, wherein the tyrosine kinase is FMS-like tyrosine kinase 3 (FLT3), FMS-like tyrosine kinase 4, vascular endothelial growth factor receptor (VEGFR), colony stimulating factor 1 receptor (CSF1R), platelet-derived growth factor receptor (PDGFR) A, PDGFR B, tyrosine-protein kinase Kit (c-KIT), c-Src (SRC), tyrosine-protein kinase Lyn (LYN) A, LYN B, rearranged during transfection tyrosine kinase (RET), lymphocyte-specific protein tyrosine kinase, Gardner-Rasheed feline sarcoma viral oncogene homolog, discoidin domain receptor 1, kinase insert domain receptor, B lymphocyte kinase, tyrosine-protein kinase Yes, Abelson murine leukemia viral oncogene homolog 1 (ABL1), tyrosine receptor kinase TRKA, TRKB, TRKC, ZAK/MLTK, IRAK4, RET V804L, RET Y791F, FLT3 D835Y, PDGFR A V561D, or ABL1 T315I.

25. The method of claim 24, wherein the tyrosine kinase is FLT3, VEGFR, or c-KIT.

26. The method of claim 25, wherein the cancer is acute myeloid leukemia, chloroma, chronic myelogenous leukemia, acute lymphoblastic leukemia, chronic lymphocytic leukemia, Hodgkin's disease, non-Hodgkin's lymphoma, B-cell lymphoma, multiple myeloma, Waldenstrom's macroglobulinemia, myelodysplastic syndrome, pancreatic cancer, bladder cancer, colorectal cancer, breast cancer, male genital tract cancer, renal cancer, hepatocellular cancer, lung cancer, ovarian cancer, cervical cancer, uterus cancer, gestational trophoblastic disease, gastric cancer, bile duct cancer, gallbladder cancer, small intestine cancer, esophageal cancer, oropharyngeal cancer, hypopharyngeal cancer, eye cancer, nerve cancer, head and neck cancer, melanoma, plasmacytoma, endocrine gland neoplasm, neuroendocrine cancer, brain tumor, bone cancer, or sarcoma.

* * * * *

UNITED STATES PATENT AND TRADEMARK OFFICE
CERTIFICATE OF CORRECTION

PATENT NO. : 10,300,061 B2  
APPLICATION NO. : 16/007417  
DATED : May 28, 2019  
INVENTOR(S) : Weir-Torn Jiaang et al.

Page 1 of 1

It is certified that error appears in the above-identified patent and that said Letters Patent is hereby corrected as shown below:

In the Claims

Column 29, Lines 28-38 Claim 19, the third compound should read as follows:

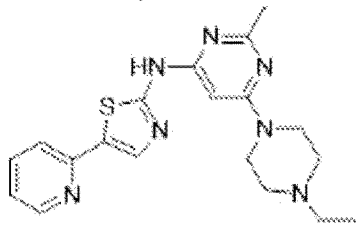

Signed and Sealed this  
Fifteenth Day of June, 2021

Drew Hirshfeld  
*Performing the Functions and Duties of the  
Under Secretary of Commerce for Intellectual Property and  
Director of the United States Patent and Trademark Office*